(12) United States Patent
Mitsumori

(10) Patent No.: US 12,033,759 B2
(45) Date of Patent: Jul. 9, 2024

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventor: Keita Mitsumori, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 271 days.

(21) Appl. No.: 16/847,893

(22) Filed: Apr. 14, 2020

(65) Prior Publication Data

US 2020/0342997 A1 Oct. 29, 2020

(30) Foreign Application Priority Data

Apr. 24, 2019 (JP) ................. 2019-083366

(51) Int. Cl.
*G16H 50/70* (2018.01)
*G16H 10/60* (2018.01)
*G16H 15/00* (2018.01)
*G16H 50/20* (2018.01)
*G16H 80/00* (2018.01)

(52) U.S. Cl.
CPC ............. *G16H 50/70* (2018.01); *G16H 10/60* (2018.01); *G16H 15/00* (2018.01); *G16H 50/20* (2018.01); *G16H 80/00* (2018.01)

(58) Field of Classification Search
CPC ........ G16H 50/70; G16H 10/60; G16H 15/00; G16H 50/20; G16H 80/00
USPC ...................................................... 705/2–4
See application file for complete search history.

(56) References Cited

U.S. PATENT DOCUMENTS

| 6,754,655 B1 * | 6/2004 | Segal ..................... G16H 50/20 |
| 8,296,247 B2 * | 10/2012 | Zhang ..................... G06N 20/00 |
| | | 706/924 |
| 8,812,241 B1 * | 8/2014 | Markin ................. G16H 10/40 |
| | | 435/7.1 |

(Continued)

FOREIGN PATENT DOCUMENTS

| JP | 10-177605 A | 6/1998 |
| JP | 2001-312558 A | 11/2001 |

(Continued)

OTHER PUBLICATIONS

Japanese Office Action dated Apr. 4, 2023 in Japanese Patent Application No. 2019-083366, 3 pages.

*Primary Examiner* — Mark Holcomb
(74) *Attorney, Agent, or Firm* — Oblon, McClelland, Maier & Neustadt, L.L.P.

(57) ABSTRACT

A medical information processing apparatus according to an embodiment includes a processing circuitry. The processing circuitry sets, as a finding, an item related to diagnosis of a subject; disposes, in an identical screen in accordance with the finding, each display region for displaying a piece of medical data related to diagnosis of the subject; and displays the medical data extracted from a first facility in the display region for displaying the medical data and displays the lacked medical data extracted from a second facility, together with information that identifies the second facility from which the extraction is made, in the display region for displaying the lacked medical data.

10 Claims, 11 Drawing Sheets

(56) References Cited

U.S. PATENT DOCUMENTS

| | | | | |
|---|---|---|---|---|
| 2002/0091687 A1* | 7/2002 | Eglington | ............... | G16H 50/20 |
| | | | | 707/999.005 |
| 2004/0019284 A1* | 1/2004 | Kawaguchi | ........ | A61B 5/02125 |
| | | | | 600/485 |
| 2004/0122702 A1* | 6/2004 | Sabol | ..................... | G06Q 10/10 |
| | | | | 706/45 |
| 2008/0242953 A1* | 10/2008 | Dew | ..................... | G16H 40/60 |
| | | | | 434/323 |
| 2009/0083072 A1* | 3/2009 | Osawa | .................... | G16H 70/60 |
| | | | | 705/2 |
| 2009/0248441 A1* | 10/2009 | Okada | .................... | G06Q 10/10 |
| | | | | 715/764 |
| 2014/0236491 A1* | 8/2014 | Katayev | ................. | G16H 70/00 |
| | | | | 702/19 |
| 2016/0253467 A1 | 9/2016 | Kitagawa et al. | | |
| 2016/0321427 A1* | 11/2016 | Bogoni | ................... | G16H 70/60 |
| 2017/0091413 A1* | 3/2017 | Kondo | ................... | G16H 30/20 |
| 2018/0350466 A1* | 12/2018 | Oliveira | ................ | G06F 40/205 |
| 2019/0156921 A1* | 5/2019 | Kohli | ..................... | G06N 20/00 |

FOREIGN PATENT DOCUMENTS

| | | |
|---|---|---|
| JP | 2003-325458 A | 11/2003 |
| JP | 2011-204055 A | 10/2011 |
| JP | 2016-162131 A | 9/2016 |
| WO | WO 2011/102309 A1 | 8/2011 |

* cited by examiner

FIG.3

| FINDING TYPE | EXTRACTION CONDITION ||
| --- | --- | --- |
| | DATA TYPE | INDEX VALUE |
| FINDING 1 | D1 | >60 |
| | D2 | <140 |
| | D3 | >70 |
| | D5 | YES |
| FINDING 2 | D1 | >100 |
| | D6 | =50 |
| | D7 | YES |
| | D9 | =78 |
| ... | ... | ... |

FIG.10

| DATA TYPE | MEDICAL FACILITY | REFERENCE RANGE |
|---|---|---|
| D1 | A | 4~200 |
|  | B | 20~100 |
|  | C | 10~150 |
|  | ... | ... |

FIG.11

| DATA TYPE | OWN FACILITY | PARTNER FACILITY | CONDITION | OPERATION |
|---|---|---|---|---|
| D1 | A | B | REFERENCE RANGES ARE DIFFERENT FROM EACH OTHER | WARNING DISPLAY |
|  | A | C | REFERENCE RANGES ARE DIFFERENT FROM EACH OTHER | NO DISPLAY |
|  | ... | ... | ... | ... |
| ... | ... | ... | ... | ... |

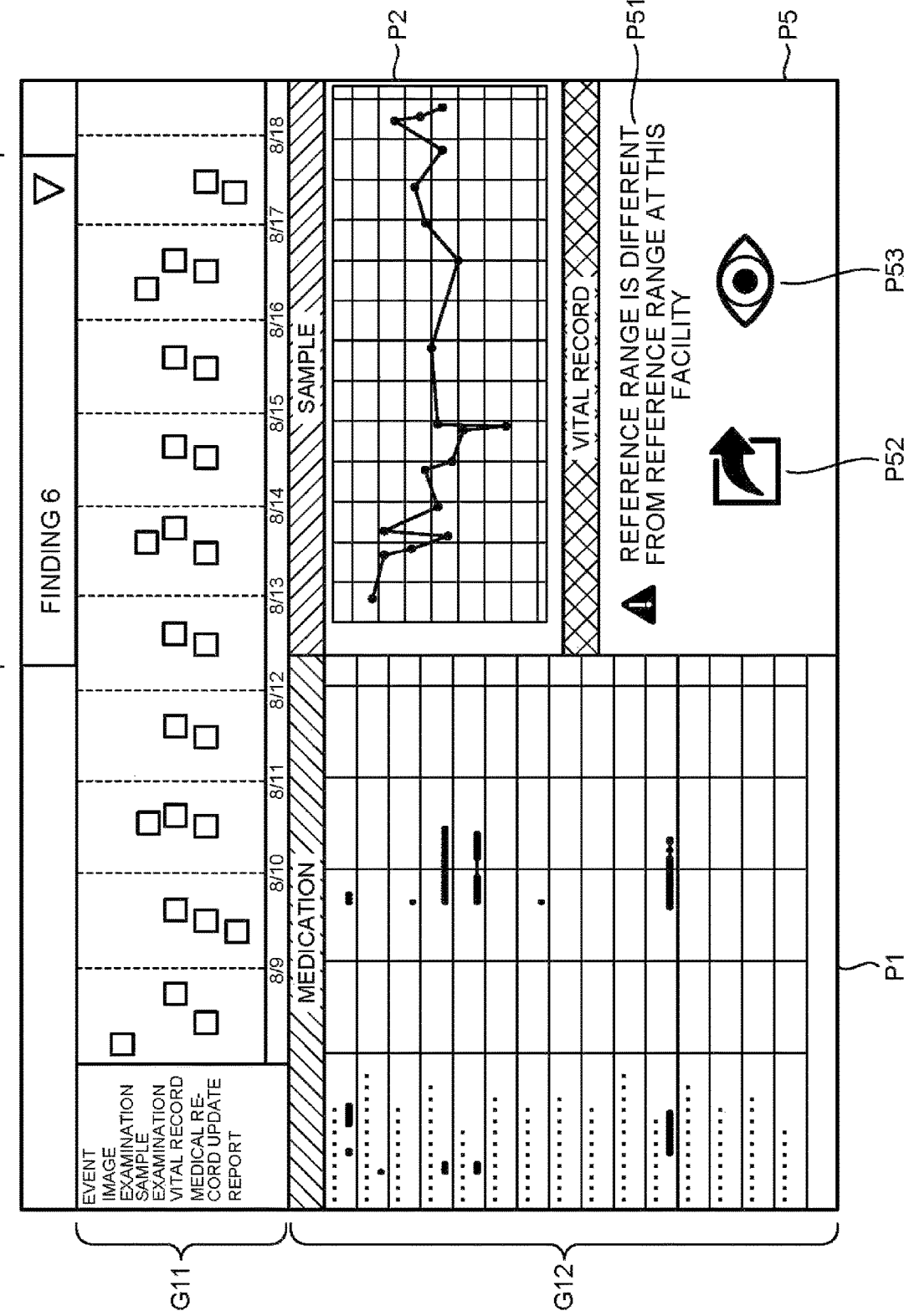

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2019-083366, filed on Apr. 24, 2019; the entire contents of which are incorporated herein by reference.

FIELD

Embodiments described herein relate to a medical information processing apparatus and a medical information processing method.

BACKGROUND

Conventional medical data used in medical practice includes various kinds of data such as image data, examination data of sample examination and the like, and medical record data. A medical professional such as a doctor performs diagnosis of a subject (for example, a patient) and the like by comprehensively analyzing the medical data.

Recently, examination of an identical subject has been performed at a plurality of medical facilities through cooperation between the medical facilities in some cases. In such a case, medical data of the subject is managed at each medical facility. Thus, a medical professional acquires, from another medical facility, lacked medical data other than medical data acquired at the own medical facility among medical data necessary for diagnosis of the subject, and performs diagnosis of the subject with the relation between the pieces of medical data taken into consideration. For example, a known method deducts a diagnostic name and the like from an anomaly finding on the subject and extracts medical data related to a result of the deduction from inside and outside a medical facility.

The above-described lacked medical data is not only acquired from another medical facility but also supplemented by performing, at the own medical facility, an examination same as that at another medical facility. In this manner, the acquisition of lacked medical data can be performed in various manners based on judgement by a medical professional, and thus has room for further improvement to increase usability.

BRIEF DESCRIPTION OF THE DRAWINGS

FIG. 3 is a diagram illustrating an exemplary data configuration of extraction condition information according to the embodiment;

FIG. 10 is a diagram illustrating an exemplary data configuration of reference range information according to a first modification;

FIG. 11 is a diagram illustrating an exemplary data configuration of operation setting information according to the first modification; and FIG. 12 is a diagram illustrating an exemplary screen displayed by the display control function according to the first modification.

DETAILED DESCRIPTION

A medical information processing apparatus according to an embodiment includes a processing circuitry. The processing circuitry sets, as a finding, an item related to diagnosis of a subject; disposes, in an identical screen in accordance with the finding, each display region for displaying a piece of medical data related to diagnosis of the subject; extracts medical data of the subject to be displayed in the display region from a first facility; extracts lacked medical data from a second facility other than the first facility when the medical data extracted from the first facility satisfies not all pieces of the medical data to be displayed in the display region; and displays the medical data extracted from the first facility in the display region for displaying the medical data and displays the lacked medical data extracted from the second facility, together with information that identifies the second facility from which the extraction is made, in the display region for displaying the lacked medical data.

The following describes a medical information processing apparatus and a medical information processing method according to the embodiment with reference to the accompanying drawings.

Figure 1:
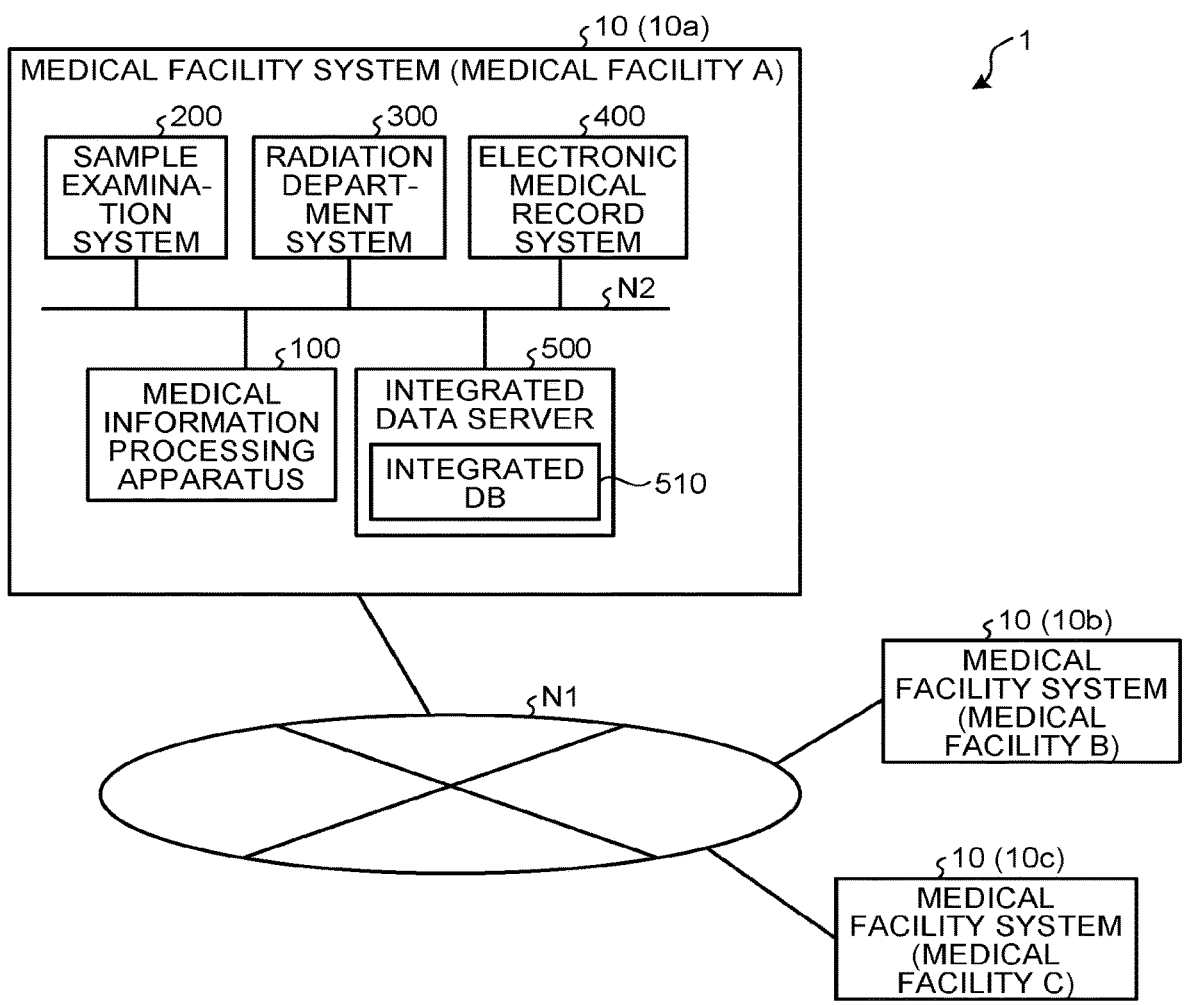
FIG. 1 is a diagram illustrating an exemplary configuration of a medical information system according to an embodiment.

FIG. 1 is a diagram illustrating an exemplary configuration of a medical information system according to the present embodiment. As illustrated in FIG. 1, this medical information system 1 includes a plurality of medical facility systems 10 (10a to 10c). The medical facility systems 10 are connected with each other to perform communication therebetween through an inter-facility network N1 such as an intranet. The number of medical facility systems 10 connected with the inter-facility network N1 is not particularly limited. Any or all of the medical facility systems 10 may be configured in a network form (cloud) using cloud computing.

Each medical facility system 10 is provided to a medical facility such as a hospital or a medical examination center. In the example illustrated in FIG. 1, the medical facility system 10a is a medical facility system of a medical facility A, the medical facility system 10b is a medical facility system of a medical facility B, and the medical facility system 10c is a medical facility system of a medical facility C. The medical facilities A to C (the medical facility systems 10a to 10c) are, for example, in the relation of regional medical cooperation and can mutually refer to medical data of a subject such as a patient.

The medical facility systems 10 includes, for example, a medical information processing apparatus 100, a sample examination system 200, a radiation department system 300, an electronic medical record system 400, and an integrated data server 500. The medical information processing apparatus 100, the sample examination system 200, the radiation department system 300, the electronic medical record system 400, and the integrated data server 500 are connected with each other to perform communication therebetween through an in-facility network N2 such as a local area network (LAN). The in-facility network N2 is connected with the inter-facility network N1 through a network instrument such as a router. The number of medical information processing apparatus 100 connected with the in-facility network N2 is not particularly limited.

The sample examination system 200 generates sample examination data related to sample examination performed on the subject and stores the generated sample examination data in a storage in the sample examination system 200. Then, the sample examination system 200 transmits sample examination data stored in the storage to the integrated data server 500. The sample examination data includes an examination result of the subject and the like as well as a patient ID for identifying the subject.

The radiation department system 300 stores image data obtained through image capturing of the subject in a storage in the radiation department system 300. In addition, the radiation department system 300 generates report data related to image examination performed on the subject and stores the generated report data in the storage in the system. For example, the radiation department system 300 includes picture archiving and communication systems (PACS) or the like. The image examination includes examination using a CT image captured by an X-ray computed tomography (CT) device, examination using an MR image captured by a magnetic resonance imaging (MRI) device, examination using an ultrasonic wave image captured by an ultrasonic wave diagnostic device, and examination using an X-ray image captured by an X-ray diagnostic device. Then, the radiation department system 300 transmits the image data and the report data stored in the storage to the integrated data server 500. The image data and the report data each include an examination result and a report of the subject and the like as well as a patient ID for identifying the subject.

The electronic medical record system 400 generates medical record data including a clinical record and a medical care record of the subject, prescription performed for the subject, and a vital record (vital data) measured from the subject, and stores the generated medical record data in a storage in the system. Then, the electronic medical record system 400 transmits the medical record data stored in the storage to the integrated data server 500. The medical record data includes the vital data and the like as well as a patient ID for identifying the subject.

The integrated data server 500 is achieved by a computer device, such as a work station or a server device, including a processing circuitry such as a processor, and a storage achieved by, for example, a semiconductor memory element such as a random access memory (RAM) or a flash memory, a hard disk, or an optical disk.

The integrated data server 500 collects various kinds of data from the sample examination system 200, the radiation department system 300, and the electronic medical record system 400, and stores the collected various kinds of data in the storage in the server. Specifically, the storage of the integrated data server 500 holds an integrated database (DB) 510 for storing and managing various kinds of data acquired from the radiation department system 300 and the electronic medical record system 400.

For example, the integrated DB 510 includes the sample examination data, the image data, the report data, and the medical record data (vital data). The sample examination data is medical data related to sample examination and acquired from the sample examination system 200. The report data and the image data are medical data related to image examination and acquired from the radiation department system 300. The medical record data is medical data related to prescription and medical care records acquired from the electronic medical record system 400.

The medical data stored in the integrated DB 510 includes information obtained by various examinations, such as numerical values (measured values), images, and clinical records, information indicating the record date and time of the obtained information, and a patient ID of the subject as described above. The patient ID may be common to the medical facilities or may be different among the medical facilities. However, in the latter case, for example, the patient IDs of an identical person at the medical facilities may be, for example, associated with one another so that the identical subject can be specified from the patient ID at each medical facility.

The medical information processing apparatus 100 acquires various kinds of medical data from the integrated data server 500 at the own medical facility and the integrated data server 500 at another medical facility, and executes information processing related to display of the acquired medical data. For example, the medical information processing apparatus 100 is achieved by a computer device such as a work station, a personal computer, or a tablet terminal.

Figure 2:
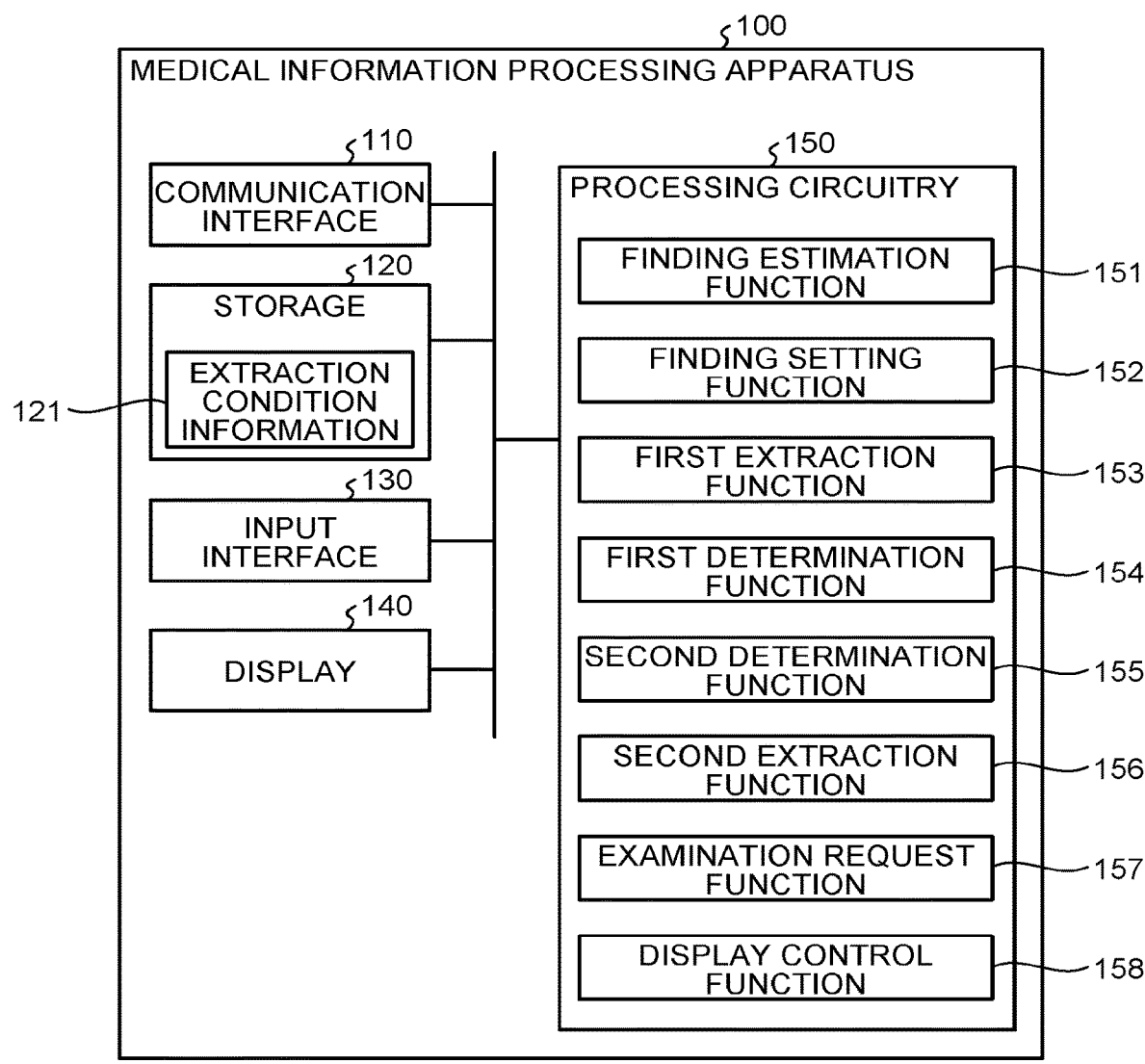
FIG. 2 is a diagram illustrating an exemplary configuration of a medical information processing apparatus according to the embodiment.

FIG. 2 is a diagram illustrating an exemplary configuration of the medical information processing apparatus 100. As illustrated in FIG. 2, the medical information processing apparatus 100 includes a communication interface 110, a storage 120, an input interface 130, a display 140, and a processing circuitry 150.

The communication interface 110 is connected with the processing circuitry 150 and controls transmission and communication of various kinds of data between the medical information processing apparatus 100 and each system. Specifically, the communication interface 110 receives medical data from each system and outputs the received medical data to the processing circuitry 150. For example, the communication interface 110 is achieved by a network card, a network adapter, a network interface controller (NIC), or the like.

The storage 120 is connected with the processing circuitry 150 and stores various kinds of data. The storage 120 also stores medical data received from each system. The storage 120 also stores extraction condition information to be described later. For example, the storage 120 is achieved by, for example, a semiconductor memory element such as a random access memory (RAM) or a flash memory, a hard disk, or an optical disk. The storage 120 is an exemplary means for achieving a storage unit.

The input interface 130 is connected with the processing circuitry 150 and receives an input operation of various instructions and various kinds of information from an operator. Specifically, the input interface 130 converts the input operation received from the operator into an electric signal and outputs the electric signal to the processing circuitry 150. For example, the input interface 130 is achieved by a truck ball, a switch button, a mouse, a keyboard, a touch pad on which the input operation is performed through touch on an operation surface, a touch screen as integration of a display screen and a touch pad, a non-contact input circuit using an optical sensor, or a voice input circuit. In the present embodiment, the input interface 130 does not necessarily need to include a physical operation component such as a mouse or a keyboard. Examples of the input interface 130 include an electric signal processing circuit configured to receive an electric signal corresponding to an input operation from an external input instrument provided separately from the device and output the electric signal to a control circuit.

The display 140 is connected with the processing circuitry 150 and displays various kinds of information and various images. Specifically, the display 140 converts data of each of various kinds of information and various images transferred from the processing circuitry 150 into a display electric signal and outputs the display electric signal. For example, the display 140 is achieved by a liquid crystal monitor, a cathode ray tube (CRT) monitor, or a touch panel.

The processing circuitry 150 controls each component of the medical information processing apparatus 100 in accordance with an input operation received from the operator through the input interface 130. Specifically, the processing circuitry 150 stores medical data output from the communication interface 110 in the storage 120. In addition, the processing circuitry 150 reads medical data from the storage 120 and displays the read medical data on the display 140. For example, the processing circuitry 150 is achieved by a processor.

The medical information processing apparatus 100 having the above-described configuration is used for various purposes by a medical professional such as a doctor. For example, the medical information processing apparatus 100 is used to display various kinds of medical data when the medical professional performs diagnosis of the subject or the like.

With the above-described medical information system 1, when an identical subject is examined at a plurality of medical facilities, medical data of the subject is managed at each medical facility. In this case, a medical professional performs diagnosis of the subject by using medical data acquired at the own medical facility as well as medical data acquired at another medical facility, and cumbersome work is needed to search the medical data managed at the other medical facility for medical data necessary for diagnosis, which is inefficient. Moreover, when all pieces of medical data related to the subject are acquired from another medical facility, the medical data cannot be displayed until the acquisition is completed, and medical data unnecessary for diagnosis is acquired, which is inefficient.

Thus, the medical information processing apparatus 100 according to the present embodiment has a function for increasing the efficiency and usability of display of medical data managed at the own medical facility and another medical facility.

Specifically, the medical information processing apparatus 100 has a finding estimation function 151, a finding setting function 152, a first extraction function 153, a first determination function 154, a second determination function 155, a second extraction function 156, an examination request function 157, and a display control function 158. The finding estimation function 151 is an exemplary finding estimation unit. The finding setting function 152 is an exemplary finding setting unit. The first extraction function 153 is an exemplary first extraction unit. The first determination function 154 and the second determination function 155 are each an exemplary determination unit. The second extraction function 156 is an exemplary second extraction unit. The examination request function 157 is an exemplary examination request unit. The display control function 158 is an exemplary disposition unit and an exemplary display control unit.

The finding estimation function 151 estimates, as a finding, an item related to diagnosis of the subject based on a physical characteristic, a chief complaint, medical data, and the like of a diagnosis target subject. The finding means, for example, a symptom (such as jaundice or fever) of the subject due to disease, illness, or the like, or a suspected disease name. The finding estimation is not limited to a particular method but may be performed by various kinds of methods.

For example, the finding estimation function 151 acquires, as a finding related to diagnosis of the subject as a diagnosis target, a symptom or a disease name corresponding to a condition of the subject based on guideline information in which combination of a physical characteristic such as age, sex, or body shape and a chief complaint is associated with a symptom, a disease name, or the like predicted from a condition of the combination. When the physical characteristic and the chief complaint of the subject are included in medical data such as the medical record data, the finding estimation function 151 may estimate a finding by using combination of the physical characteristic and the chief complaint included in the medical data.

Alternatively, for example, the finding estimation function 151 may estimate a finding by using an estimation model such as a machine learning model obtained by learning the relation between medical data of each of a plurality of subjects and a diagnosis result (finding) or a simulator. In this case, the finding estimation function 151 inputs medical data of a subject as a diagnosis target into the estimation model and acquires, as a finding, a diagnosis result output from the estimation model.

The number of findings estimated by the finding estimation function 151 is not limited to one but may be equal to or larger than two. For example, the finding estimation function 151 may select a predetermined number (for example, three) of findings with highest validities.

The finding setting function 152 sets item related to diagnosis of a subject as a finding. For example, when one of findings estimated by the finding estimation function 151 is selected through the input interface 130 or the like, the finding setting function 152 sets the selected finding as a processing target. Alternatively, when a finding is input through the input interface 130 or the like, the finding setting function 152 sets the input finding as a processing target.

The first extraction function 153 extracts, from among medical data (hereinafter referred to as first medical data) of a diagnosis target subject managed at the integrated data server 500 of the own medical facility, the first medical data related to a finding set by the finding setting function 152. Specifically, the first extraction function 153 extracts the first medical data satisfying a condition on the finding set by the finding setting function 152 from among the first medical data of the subject managed at the own medical facility based on extraction condition information 121 in which a condition on medical data as a display target is defined for each finding.

FIG. 3 is a diagram illustrating an exemplary data structure of the extraction condition information 121. As illustrated in FIG. 3, the extraction condition information 121 stores, for each finding type, a condition (extraction condition) for medical data as a display target, in other words, an extraction target in association with the finding type.

The extraction condition is expressed by, for example, a data type or a pair of the data type and an index value. FIG. 3 illustrates an example in which the extraction condition is expressed by a pair of the data type and the index value. The data type means, for example, the examination type of an examination result included in medical data. For example, the data type is set to be the type of quantitative data, such as the number of leucocytes or γ-GPT (glutamate pyruvate transaminase), obtained through a sample examination. Alternatively, for example, the data type is set to be the type of qualitative data such as a particular symptom (such as jaundice), a medical history, or an allergy type.

The index value stores, for example, the index value of a data type as a basis of a finding. For example, when the data type is quantitative data, a numerical value range or the like is set. When the data type is qualitative data, a value indicating the existence of an item corresponding to the qualitative data, a negative or positive result, or the like is set.

The number of extraction conditions set to each finding is not particularly limited. For example, in the extraction condition information 121 in FIG. 3, four extraction conditions with the data types of D1, D2, D3, and D5 are set as extraction conditions on medical data related to "Finding 1". In addition, four extraction conditions with the data type of D1, D6, D7, and D9 are set as extraction conditions on medical data related to "Finding 2".

The first extraction function 153 extracts, based on an extraction condition on the finding set by the finding setting function 152, the first medical data satisfying the extraction condition from among the first medical data of the diagnosis target subject managed at the integrated data server 500 of the own medical facility. For example, when "Finding 1" is set by the finding setting function 152, the first extraction function 153 searches for and extracts, for each of the four extraction conditions associated with "Finding 1", the first medical data satisfying the extraction condition.

The first determination function 154 determines whether the first medical data extracted by the first extraction function 153 satisfies all extraction conditions corresponding to the finding set by the finding setting function 152.

For example, as for the extraction conditions for "Finding 1" illustrated in FIG. 3, when the data type of the first medical data extracted by the first extraction function 153 is D1, D3, and D5, the first determination function 154 determines that medical data satisfying the extraction condition on the data type D2 is lacked. For example, as for the extraction conditions for "Finding 2", when the data type of the first medical data extracted by the first extraction function 153 is D1, D6, and D7, the first determination function 154 determines that medical data satisfying the extraction condition on the data type D9 is lacked.

When the first determination function 154 has determined that medical data is lacked, the second determination function 155 determines whether medical data satisfying the lacked extraction condition is available at another medical facility (medical facility system 10). Specifically, the second determination function 155 determines whether medical data of the diagnosis target subject is available in medical data managed at the integrated data server 500 of another medical facility system 10. When no medical data of the subject is available in the medical data managed at the integrated data server 500 of the other medical facility system 10, it is determined that no medical data satisfying the lacked extraction condition is available.

When it is determined that medical data of the diagnosis target subject is available in the medical data managed at the integrated data server 500 of the other medical facility system 10, the second determination function 155 searches the medical data of the subject for medical data satisfying the lacked extraction condition. When no medical data satisfying the extraction condition has been found, the second determination function 155 determines that no medical data satisfying the lacked extraction condition is available. When medical data satisfying the extraction condition has been found, the second determination function 155 determines that medical data satisfying the lacked extraction condition is available at the other medical facility. In this case, the second determination function 155 may notify the second extraction function 156 of the storage destination of the medical data satisfying the extraction condition.

The second extraction function 156 extracts, from among medical data (hereinafter referred to as second medical data) of the subject managed at the other medical facility (medical facility system 10), the second medical data related to a finding set by the finding setting function 152. Specifically, when the second determination function 155 has determined that medical data satisfying the lacked extraction condition is available at the other medical facility, the second extraction function 156 extracts the second medical data satisfying the lacked extraction condition from among the second medical data of the subject managed at the other medical facility.

For example, as for the extraction conditions for "Finding 1" illustrated in FIG. 3, the data type of the first medical data extracted by the first extraction function 153 is D1, D3, and D5, and the second determination function 155 has determined that medical data satisfying the extraction condition on the data type D2 is available at another medical facility. In this case, based on a result of the determination by the second determination function 155, the second extraction function 156 extracts the second medical data satisfying the extraction condition on the data type D2 from among the second medical data of the diagnosis target subject managed at the other medical facility. For example, as for the extraction conditions for "Finding 2", the data type of the first medical data extracted by the first extraction function 153 is D1, D6, and D7, and the second determination function 155 has determined that medical data satisfying the extraction condition on the data type D9 is available at another medical facility. In this case, based on a result of the determination by the second determination function 155, the second extraction function 156 extracts the second medical data satisfying the extraction condition on the data type D9 from among the second medical data of the diagnosis target subject managed at the other medical facility.

The timing at which the second extraction function 156 starts the second medical data extraction is not particularly limited. The second extraction function 156 may start the second medical data extraction from another medical facility, for example, when its availability is confirmed by the second determination function 155. Alternatively, the second extraction function 156 may start the second medical data extraction from another medical facility, for example, when acquisition or display of the second medical data is instructed by a user through the input interface 130 or the like. Alternatively, for example, a condition for starting the second medical data extraction may be optionally set through the input interface 130 or the like, and the extraction may be started based on the set condition.

The examination request function 157 executes processing for requesting an examination related to the lacked extraction condition determined to be unavailable by the second determination function 155. Specifically, when a request for an examination related to the lacked extraction condition is received from the user through the input interface 130 or the like, the examination request function 157 transmits, to the own medical device system that executes the examination, examination request information for requesting an examination of the subject. The examination request information includes, for example, the patient ID of the diagnosis target subject, the data type of the lacked extraction condition, and a medical professional ID of a medical professional having requested the examination.

The display control function 158 controls a screen displayed on the display 140 of the medical information processing apparatus 100. Specifically, when the patient ID of a diagnosis target subject is input through the input interface 130 or the like, the display control function 158 controls the display 140 to display a screen for displaying medical data related to the subject having the patient ID.

Figure 4:
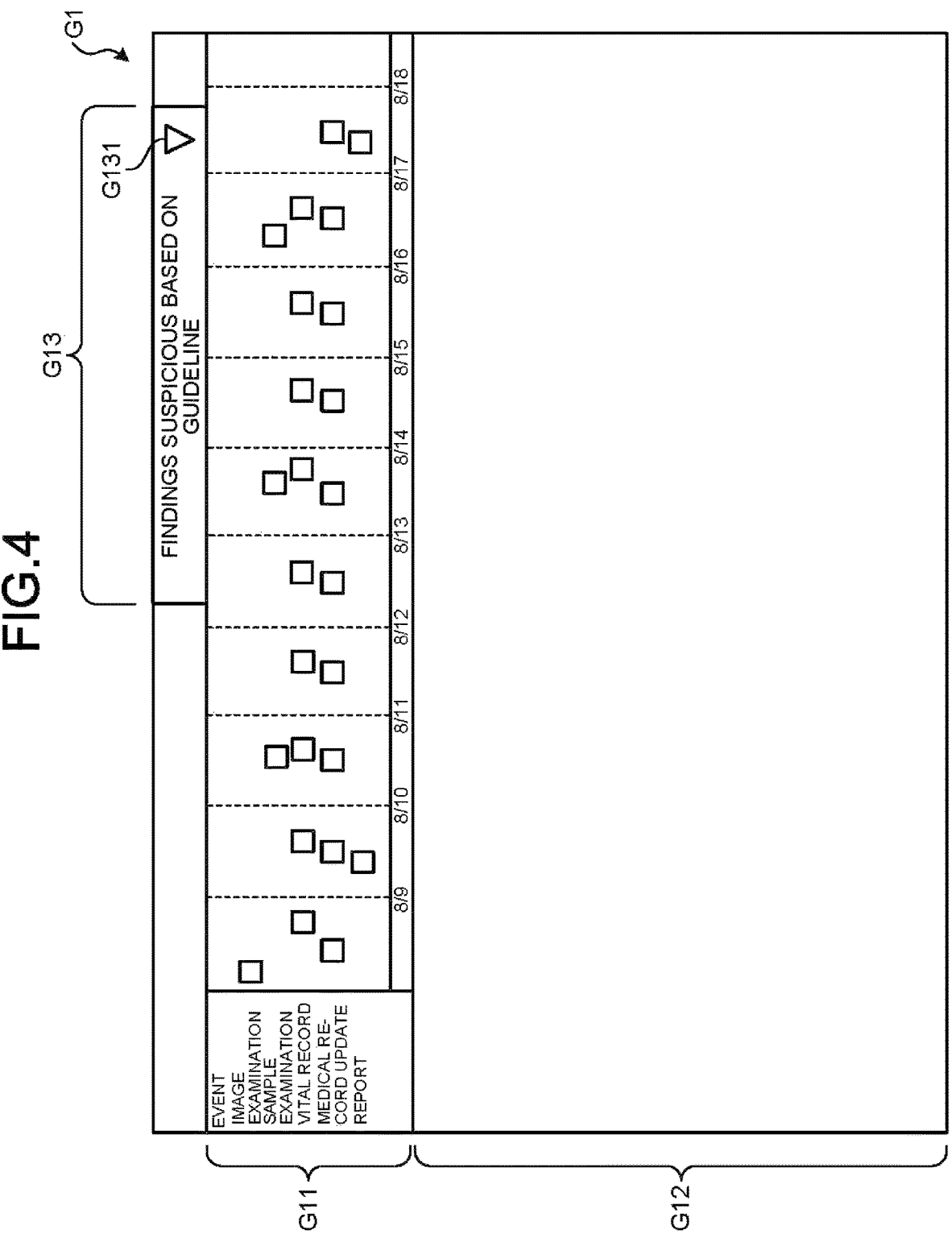
FIG. 4 is a diagram illustrating an exemplary screen displayed by a display control function according to the embodiment.

FIG. 4 is a diagram illustrating an exemplary screen displayed by the display control function 158. As illustrated in FIG. 4, a screen G1 includes a timeline display region G11, a data display region G12, and a finding selection region G13.

In the timeline display region G11, each clinical treatment performed on the diagnosis target subject at the own medical facility is displayed as an event in a temporally sequential manner. The events are, for example, a sample examination acquisition event ("sample examination") by the sample examination system 200, report-data and image-data acquisition events ("image examination" and "report") by the radiation department system 300, medical-record-data and vital-data acquisition events ("medical record update" and "vital record") by the electronic medical record system 400. For example, the display control function 158 disposes and displays, in a temporally sequential manner, figures that symbolically express the contents of an event of clinical treatment on a patient.

When an operation that specifies any event displayed in the timeline display region G11 is received through the input interface 130 or the like, the display control function 158 refers to the integrated data server 500 and acquires medical data corresponding to the specified event. When an operation that specifies any time point or duration in a display duration displayed in the timeline display region G11 is received through the input interface 130 or the like, the display control function 158 refers to the integrated data server 500 and acquires medical data corresponding to an event performed at the specified time point or in the specified duration. Then, the display control function 158 displays the contents of the acquired medical data in the data display region G12.

For example, when the medical data corresponding to the event is image data, the display control function 158 displays an image represented by the image data in the data display region G12. Alternatively, for example, when the medical data corresponding to the specified event is sample examination data, vital data, or the like, the display control function 158 displays a measured value obtained at the specified time point or in the specified duration or a graph illustrating change of the measured value in the data display region G12.

In the data display region G12, pieces of medical data are displayed in a display region (hereinafter also referred to as a panel) smaller than the data display region G12. Accordingly, in the data display region G12, a plurality of pieces of medical data can be displayed in an identical screen.

Display arrangement of the screen G1 is not particularly limited but may be optionally set. For example, the size of a panel may be a fixed value determined for each data type of medical data or may be dynamically changed in accordance with the number of pieces of medical data to be displayed. The type of image data displayed in each panel may be set in advance or may be dynamically allocated based on a predetermined priority or the like. The number of panels displayable in the data display region G12 is not particularly limited but may be a fixed value or may be dynamically changed in accordance with the number of pieces of medical data to be displayed or the like. In addition, the panel arrangement is not particularly limited but may be fixed or may be dynamically changed in accordance with the number of pieces of medical data to be displayed or the like.

In the finding selection region G13, findings estimated by the finding estimation function 151 are presented as selection candidates. The finding selection region G13 can be operated through the input interface 130 or the like. For example, when an operation element G131 in the finding selection region G13 is operated, the display control function 158 expands the finding selection region G13 downward to display a list of the findings estimated by the finding estimation function 151 as illustrated in FIG. 5.

Figure 5:
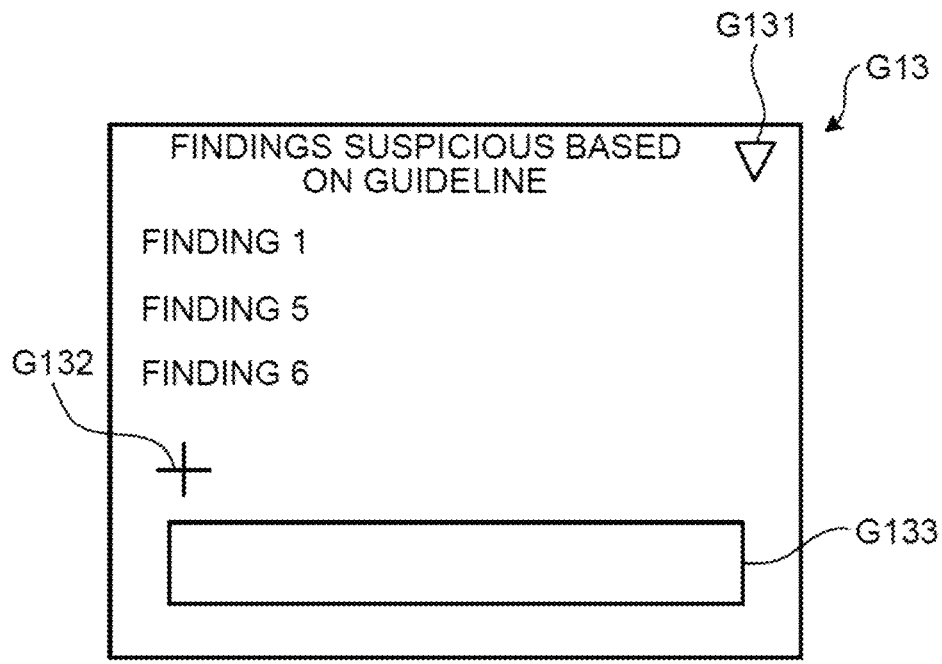
FIG. 5 is a diagram for description of an operation method of a finding set region illustrated in FIG. 4.

FIG. 5 is a diagram for description of a method of operating the finding selection region G13 illustrated in FIG. 4. As illustrated in FIG. 5, in the finding selection region G13, each finding estimated by the finding estimation function 151 is displayed in a selectable state. FIG. 5 illustrates an example in which the three findings of "Finding 1", "Finding 5", and "Finding 6" are estimated. When any one of the findings displayed in the finding selection region G13 is selected, the finding setting function 152 sets the selected finding as a processing target.

In the finding selection region G13, a finding can be additionally input through a manual operation. Specifically, when an operation on an operation element G132 is received in the finding selection region G13, the display control function 158 displays an input region G133 through which a finding can be additionally input in the finding selection region G13. When a finding is input in the input region G133, the finding setting function 152 sets the input finding as a processing target.

In this manner, the user of the medical information processing apparatus 100 can select a finding estimated by the finding estimation function 151 or an optional finding as a finding related to the subject through the finding selection region G13.

Upon the finding setting by the finding setting function 152, the display control function 158 disposes each panel for displaying a piece of medical data related to diagnosis of the subject in the data display region G12 in accordance with the set finding. For example, when "Finding 1" illustrated in FIG. 3 is set, the display control function 158 disposes panels for displaying pieces of medical data corresponding to the extraction conditions D1, D2, D3, and D5 in the data display region G12. In addition, the first extraction function 153 starts extraction of the first medical data related to the set finding from among the first medical data of the diagnosis target subject managed at the integrated data server 500 of the own medical facility. The first determination function 154, the second determination function 155, and the second extraction function 156 sequentially operate in accordance with a result of the extraction of the first medical data by the first extraction function 153.

When a particular duration is specified through the timeline display region G11 or the like, the finding estimation function 151, the first extraction function 153, the first determination function 154, the second determination function 155, and the second determination function 155 may perform finding estimation and search and extraction of medical data satisfying the extraction condition within the range of medical data corresponding to any event performed in the specified duration. Accordingly, for example, the user of the medical information processing apparatus 100 can perform diagnosis of the subject only based on medical data acquired in a particular duration such as a relatively recent duration, which can lead to increase of usability.

The display control function 158 displays medical data satisfying the extraction condition on a finding set by the finding setting function 152 in a panel disposed in the data display region G12 based on a result of the operation of the first extraction function 153, the first determination function 154, the second determination function 155, and the second extraction function 156. Specifically, the display control function 158 displays the first medical data extracted by the first extraction function 153 in a panel corresponding to the extraction condition on the first medical data. In addition, the display control function 158 controls display of the second medical data in accordance with a result of the determination by the first determination function 154 and the second determination function 155.

For example, when the first determination function 154 has determined that the first medical data extracted by the first extraction function 153 satisfies all extraction conditions, the display control function 158 displays only the first medical data extracted by the first extraction function 153 in a corresponding panel disposed in the data display region G12.

For example, when the second determination function 155 has determined that medical data satisfying the lacked extraction condition is available at another medical facility, the display control function 158 displays pieces of first medical data extracted by the first extraction function 153 in a panel corresponding to the extraction condition on the first medical data. In addition, the display control function 158 displays information (hereinafter referred to as display check information) for prompting the user to check whether to display the second medical data extracted by the second extraction function 156 in a panel corresponding to the extraction condition on the second medical data.

Figure 6:
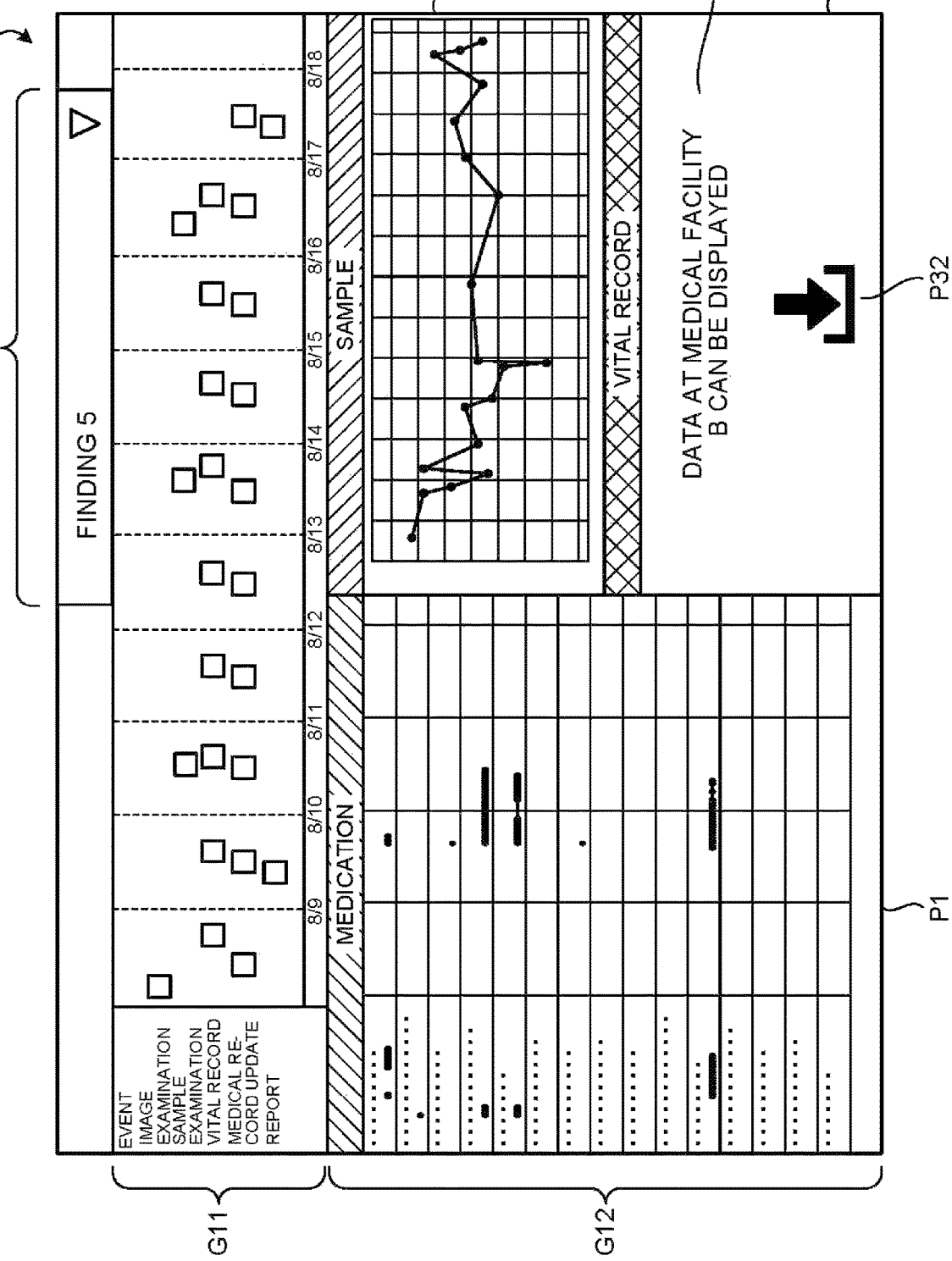
FIG. 6 is a diagram illustrating an exemplary screen displayed by the display control function according to the embodiment.

FIG. 6 is a diagram illustrating an exemplary screen displayed by the display control function 158 in a state in which the display check information is displayed in the data display region G12. The display control function 158 displays two pieces of the first medical data extracted by the first extraction function 153 in corresponding panels P1 and P2, respectively, in the data display region G12. FIG. 6 illustrates an example in which "Finding 5" is selected in the finding selection region G13 and a medication record and sample examination data are displayed in the corresponding panels P1 and P2 as the first medical data satisfying the extraction condition on "Finding 5".

In addition, the display control function 158 displays the display check information for checking whether to display medical data available at another medical facility in a panel P3 corresponding to the extraction condition on the medical data based on a result of the determination by the second determination function 155. Specifically, the display control function 158 displays, as the display check information in the panel P3, a message P31 giving notification that medical data (vital data) satisfying the lacked extraction condition is available at another medical facility and can be displayed. The message P31 includes the name of a medical facility (the medical facility B) as the extraction source of the medical data.

In addition, the display control function 158 displays, as the display check information in the panel P3, an operation element P32 for instructing display (or acquisition) of the medical data managed at the other medical facility. The user of the medical information processing apparatus 100 checks the message P31 displayed as the display check information, and when desiring display of the medical data, can instruct the display by operating the operation element P32.

In this manner, before display of the second medical data, the medical information processing apparatus 100 prompts the user of the medical information processing apparatus 100 to check intention for the display. Accordingly, for example, when the user of the medical information processing apparatus 100 performs diagnosis or the like only with medical data at the own medical facility, the second medical data can be prevented from being unnecessarily displayed. Thus, the medical information processing apparatus 100 can increase the usability of acquisition and display of lacked medical data.

The medical information processing apparatus 100 displays the first medical data in the screen G1 and also displays, in the identical screen G1, the message P31 that the first medical data is available at another medical facility and the operation element P32. Accordingly, the medical information processing apparatus 100 allows the user of the medical information processing apparatus 100 to recognize what kind of medical data is lacked, whether the lacked medical data is available at another medical facility, and the like, which can lead to increase of usability. In addition, since the operation element P32 is displayed in the identical screen for the first medical data, the user of the medical information processing apparatus 100 can easily perform an operation related to acquisition of the lacked medical data without switching screens, which can lead to increase of usability.

Figure 7:
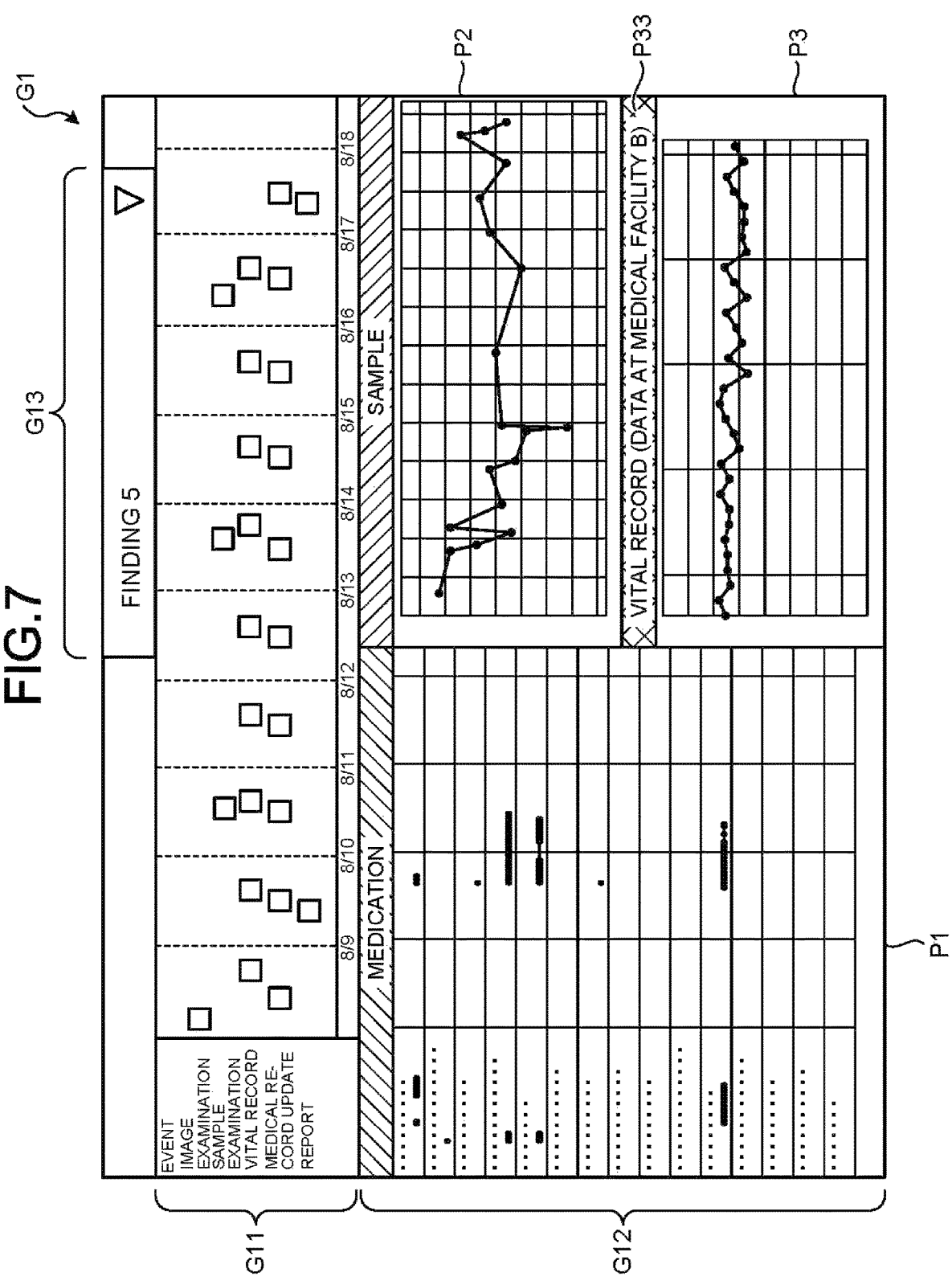
FIG. 7 is a diagram illustrating an exemplary screen displayed by the display control function according to the embodiment.

When an operation is received on the operation element P32, the display control function 158 displays the second medical data extracted from another medical facility (the medical facility B) by the second extraction function 156 in the panel P3 corresponding to the extraction condition on the second medical data as illustrated in FIG. 7. The second extraction function 156 may start extraction of the second medical data in accordance with an operation on the operation element P32.

FIG. 7 is a diagram illustrating an exemplary screen displayed by the display control function 158 in a state in which the second medical data is displayed. Specifically, when an instruction to display the second medical data is received, the display control function 158 deletes the display check information and displays the second medical data extracted by the second extraction function 156 in the panel P3. In addition, the display control function 158 displays extraction source information P33 indicating another medical facility (the medical facility B) as the extraction source of the second medical data in association with the panel P3. Accordingly, the display control function 158 displays the second medical data and the extraction source information P33 in association with each other in the panel P3.

Accordingly, the user of the medical information processing apparatus 100 can easily check from which medical facility the medical data is acquired by looking at the extraction source information P33. Since the first medical data extracted from the own medical facility and the second medical data extracted from another medical facility are displayed in an identical screen, the user of the medical information processing apparatus 100 can easily check the relation between the first medical data and the second medical data. Thus, the medical information processing apparatus 100 can increase usability of medical data display.

When the second extraction function 156 extracts a plurality of pieces of the second medical data, the display control function 158 may dispose a panel for each of the extraction conditions for the extracted pieces of the second medical data or may display the pieces of the second medical data in an identical panel. The latter case is effective, for example, when pieces of the second medical data (numerical data) of an identical data type are displayed in a graph format or the like. In addition, for example, when the second extraction function 156 extracts the second medical data from other medical facilities different from each other or extracts a plurality of pieces of the second medical data of data types different from each other from an identical medical facility, the display control function 158 may display the display check information for each medical facility or each data type.

In FIGS. 6 and 7, the display control function 158 displays the second medical data when the display is instructed by the user, but the present disclosure is not limited thereto, and the second medical data may be immediately displayed without display of the display check information.

Figure 8:
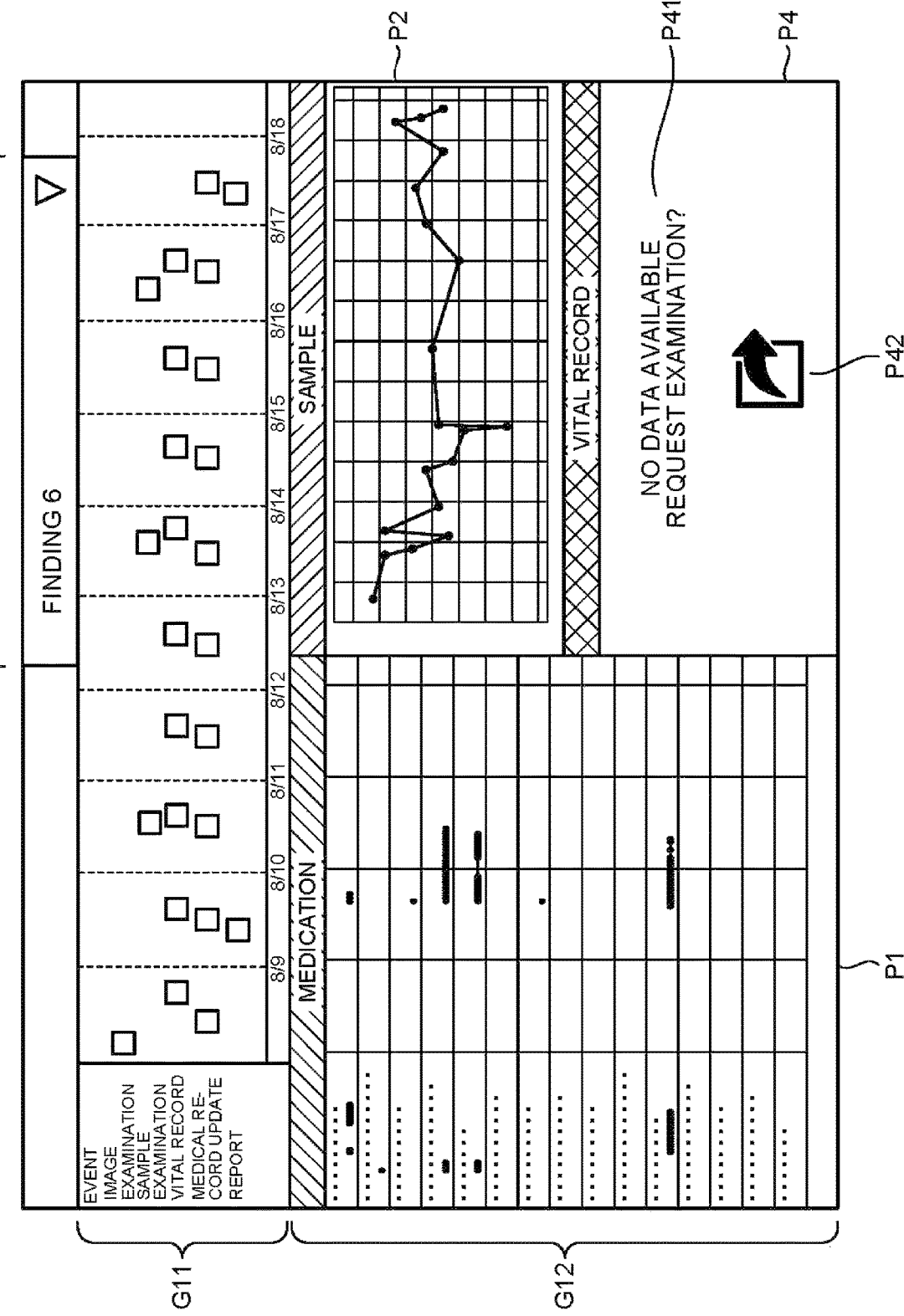
FIG. 8 is a diagram illustrating an exemplary screen displayed by the display control function according to the embodiment.

For example, when the second determination function 155 has determined that medical data satisfying a lacked extraction condition is unavailable at another medical facility, the display control function 158 displays notification information giving notification that the medical data satisfying the extraction condition is lacked in a panel disposed for the extraction condition on the medical data as illustrated in FIG. 8.

FIG. 8 is a diagram illustrating an exemplary screen displayed by the display control function 158 in a state in which the notification information is displayed in the data display region G12. Similarly to FIG. 6, the display control function 158 displays two pieces of the first medical data extracted by the first extraction function 153 in the corresponding panels P1 and P2, respectively, in the data display region G12. FIG. 8 illustrates an example in which "Finding 6" is selected in the finding selection region G13 and a medication record and sample examination data are displayed in the panels P1 and P2 as the first medical data satisfying the extraction condition on "Finding 6".

In addition, the display control function 158 displays the notification information giving notification that medical data satisfying the extraction condition is lacked in a panel P4 corresponding to the extraction condition on the lacked medical data based on a result of the determination by the second determination function 155. Specifically, the display control function 158 displays, as the notification information in the panel P4, a message P41 giving notification that no medical data (vital data) is available and checking whether to request an examination.

In addition, the display control function 158 displays, as the notification information in the panel P4, an operation element P42 for requesting an examination. The user of the medical information processing apparatus 100 checks the message P41 displayed as the notification information, and when desiring an examination of the subject, can request the examination by operating the operation element P42. The notification information is not limited to the example illustrated in FIG. 8.

When an operation on the operation element P42 is received, the examination request function 157 transmits the examination request information to a system related to the data type of the extraction condition on medical data determined to be lacked by the first determination function 154 or the second determination function 155. Accordingly, the user of the medical information processing apparatus 100 can request the own medical facility for an examination related to the lacked medical data.

In this manner, in the medical information processing apparatus 100, the message P41 and the operation element P42 for requesting an examination are displayed in the identical screen in which the first medical data is displayed, more specifically, in a display form (the panel P4) same as those of the panels P1 and P2. Accordingly, with the medical information processing apparatus 100, lack of medical data can be intuitively recognized by the user of the medical information processing apparatus 100, which can lead to increase of usability. Since the operation element P42 is displayed in a display form same as those of the panels P1 and P2, the user of the medical information processing apparatus 100 can easily operate the operation element P42, which can lead to increase of operability.

Figure 9:
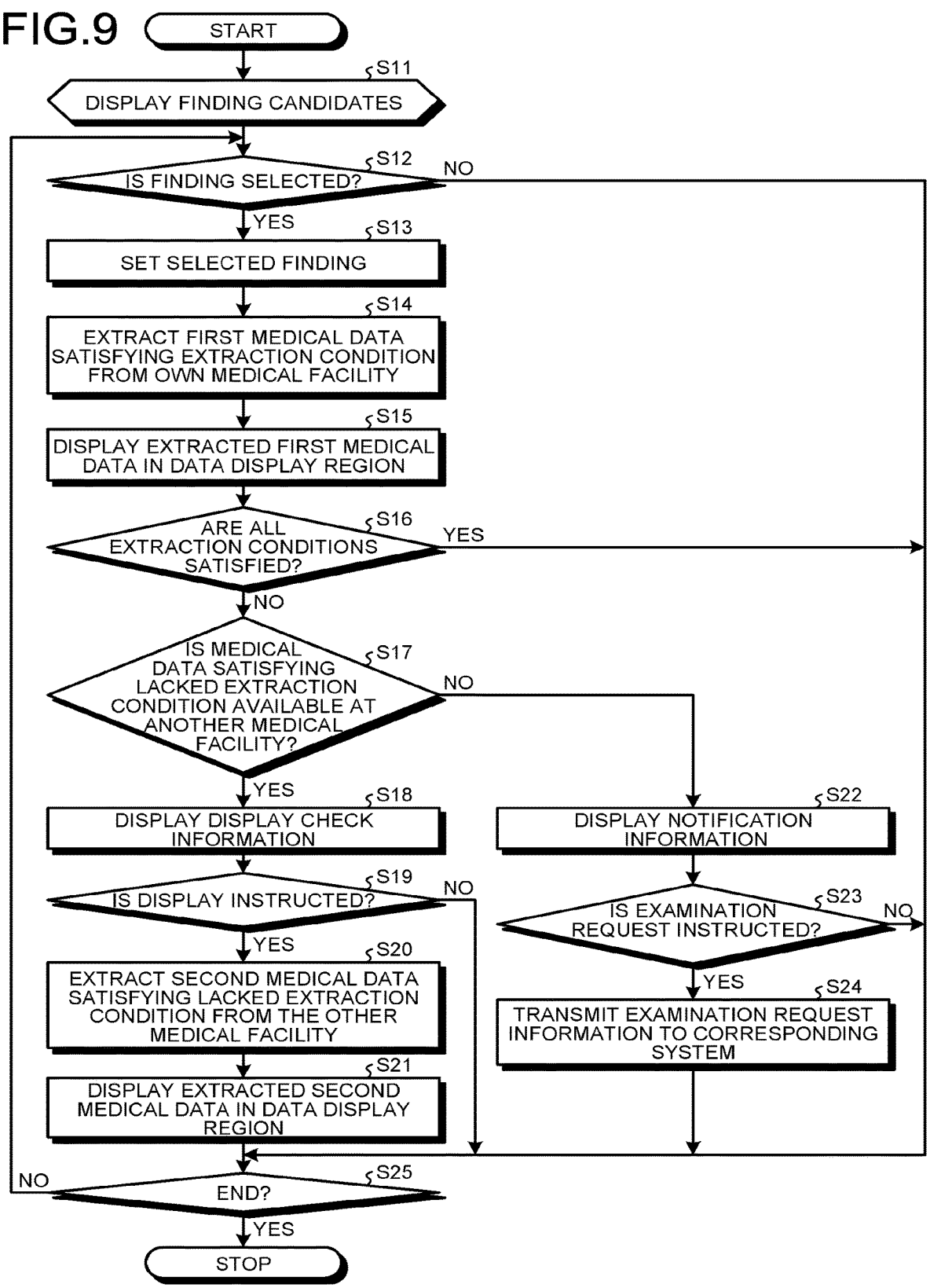
FIG. 9 is a flowchart illustrating exemplary processing executed by the medical information processing apparatus according to the embodiment.

The following describes exemplary operation of the above-described medical information processing apparatus 100 with reference to FIG. 9. FIG. 9 is a flowchart illustrating exemplary processing executed by the medical information processing apparatus 100. The present processing assumes that the screen illustrated in FIG. 4 is being displayed on the display 140 after the patient ID of a subject is input.

First, the display control function 158 displays findings estimated by the finding estimation function 151 in the finding selection region G13 as selection candidates (step S11). The finding setting function 152 determines whether a finding is selected (or input) through the finding selection region G13 (step S12). If no finding is selected (No at step S12), the process proceeds to step S25. If a finding is selected (Yes at step S12), the finding setting function 152 sets the selected finding as a processing target (step S13).

Subsequently, the first extraction function 153 extracts the first medical data satisfying the extraction condition on the finding set at step S13 from among the first medical data of the subject managed at the integrated data server 500 of the own medical facility (step S14). The display control function 158 displays the first medical data extracted at step S14 in a corresponding panel in the data display region G12 (step S15).

Subsequently, the first determination function 154 determines whether the first medical data extracted at step S14 satisfies all extraction conditions (step S16). If having determined that all extraction conditions are satisfied (Yes at step S16), the first determination function 154 moves the process to step S25. If having determined that not all extraction conditions are satisfied (No at step S16), the first determination function 154 moves the process to step S17.

At step S17, the second determination function 155 determines whether medical data of the subject satisfying a lacked extraction condition is available at the integrated data server 500 of another medical facility (step S17). If it is determined that the medical data is available at another medical facility (Yes at step S17), the display control function 158 displays, in a corresponding panel in the data display region G12, the display check information for prompting the user to check whether to display the medical data (step S18). Then, the second extraction function 156 determines whether display of the medical data is instructed based on the display check information displayed at step S18 (step S19).

If display of the medical data is instructed (Yes at step S19), the second extraction function 156 extracts the second medical data satisfying the lacked extraction condition from among the second medical data of the subject managed at the integrated data server 500 of the other medical facility (step S20). Then, the display control function 158 displays the second medical data extracted at step S20 in a corresponding panel in the data display region G12 (step S21), and the process proceeds to step S25. If no display is instructed at step S19 (No at step S19), the second medical data is not displayed and the process proceeds to step S25.

If it is determined at step S17 that no medical data satisfying the lacked extraction condition is available at another medical facility (No at step S17), the display control function 158 displays the notification information giving notification that medical data satisfying the extraction condition is lacked in a corresponding panel in the data display region G12 (step S22). Then, the examination request function 157 determines whether an examination request is instructed based on the notification information displayed at step S22 (step S23).

If the examination request is instructed (Yes at step S23), the examination request function 157 transmits the examination request information to a system corresponding to an examination on the lacked extraction condition (data type) from among the second medical data of the subject managed at the integrated data server 500 of the other medical facility (step S24), and the process proceeds to step S25. If no examination request is instructed at step S23 (No at step S23), the examination request information is not transmitted and the process proceeds to step S25.

At step S25, the display control function 158 determines whether end of the process is instructed by the user of the medical information processing apparatus 100 (step S25). If the end is not instructed (No at step S25), the display control function 158 returns the process to step S12 to continue display of medical data. If the end is instructed (Yes at step S25), the display control function 158 ends the present processing.

As described above, in the present embodiment, when a finding related to the subject is set, medical data related to the finding is extracted from among medical data of the subject managed at the own medical facility and another medical facility and is displayed in the identical screen. Accordingly, the user of the medical information processing apparatus 100 can easily check the medical data related to the finding among medical data of the subject managed at the own medical facility and the other medical facility. Thus, in the present embodiment, the usability of display of pieces of medical data acquired from a plurality of facilities can be increased, and the efficiency of diagnosis work can be increased.

In addition, in the present embodiment, when medical data satisfying the extraction condition is lacked, the user of the medical information processing apparatus 100 is notified of the lack and provided with an operation element related to acquisition of the lacked medical data. Accordingly, the user of the medical information processing apparatus 100 can easily instruct acquisition of the lacked medical data from another medical facility or request an examination to the own medical facility, and thus the usability of acquisition of the lacked medical data can be increased.

The above-described embodiment may be modified as appropriate by changing some of the components and functions of the medical information processing apparatus 100. The following describes modifications of the above-described embodiment. The description is mainly made on any difference from the above-described embodiment, and detailed description of any feature common to an already described content is omitted. The modifications described below may be individually performed or may be performed in combination as appropriate.

First Modification

In the above-described embodiment, the display control function 158 directly displays the second medical data extracted from another medical facility, but the present disclosure is not limited thereto, and for example, the display form of measured values and the like may be changed and displayed.

For example, the reference range of a measured value (data value) related to diagnosis such as normal-abnormal determination or severity determination differs between medical facilities in some cases. In such a case, the display control function 158 may change the display form of the second medical data in accordance with the reference range of the measured value at the own medical facility based on the reference ranges used at the own medical facility and another medical facility from which the second medical data is extracted.

Specifically, the display control function 158 refers to reference range information 122 illustrated in FIG. 10 and specifies the reference ranges used at the own medical facility and the other medical facility. FIG. 10 is a diagram illustrating an exemplary data configuration of the reference range information 122. The reference range information 122 may be stored in the storage 120 of the medical information processing apparatus 100 or may be stored in the storage of the integrated data server 500 or the like.

As illustrated in FIG. 10, the reference range information 122 stores, for each data type of medical data, the reference range used at each medical facility in association with the data type. For example, when the own medical facility is the medical facility A and the other medical facility from which the second medical data is extracted is the medical facility B, the reference range information 122 changes the display form of the second medical data based on the reference ranges at both facilities. The change of the display form is not limited to a particular method but may be performed by various kinds of methods.

For example, the display control function 158 may display, in addition to the second medical data, auxiliary information clearly indicating the reference ranges at the own medical facility and the other medical facility. For example, the display control function 158 may correct the measured value included in the second medical data based on the difference between a first reference range and a second reference range and display the corrected measured value.

In this manner, in the present modification, the display form of the second medical data is changed based on the reference ranges at the own medical facility and the other medical facility. Accordingly, the user of the medical information processing apparatus 100 can perform diagnosis work by using the second medical data changed in accordance with the reference range at the own medical facility, and thus the efficiency of diagnosis work can be increased.

The operation of the display control function 158 when the reference range at the own medical facility and the reference range at the other medical facility are different from each other is not limited to the above example, but the display control function 158 may be controlled to perform other operation. In this case, for example, the operation of the display control function 158 may be controlled based on operation setting information 123 as illustrated in FIG. 11. FIG. 11 is a diagram illustrating an exemplary data configuration of the operation setting information 123. The operation setting information 123 may be stored in the storage 120 of the medical information processing apparatus 100 or may be stored in the storage of the integrated data server 500 or the like.

As illustrated in FIG. 11, the operation setting information 123 stores, for each data type of medical data, combination of the own medical facility (own facility) and the other medical facility (partner facility) from which the second medical data is extracted, a condition, and operation in association with the data type. The "condition" may be set to be, for example, a case in which the reference ranges are different from each other or a case in which the difference between the reference ranges exceeds a threshold. The "operation" defines the operation of the display control function 158 when the corresponding "condition" is met. For example, the "operation" may be defined to be to perform warning display giving notification that the reference ranges are different from each other at display of the second medical data, or may be defined to be not to display the second medical data.

When the operation setting information 123 is used, the display control function 158 controls display of the second medical data based on the contents of the "condition" and the "operation" that correspond to the data type of the second medical data extracted by the second extraction function 156 and to a pair of the own medical facility and the other medical facility from which the second medical data is extracted. Contents set to the "condition" and the "operation" are not limited to the example in FIG. 11.

FIG. 12 is a diagram illustrating an exemplary screen displayed by the display control function 158 in exemplary operation based on the operation setting information 123. In FIG. 12, the above-described warning display is performed as the "operation" when the reference ranges at the own medical facility and the other medical facility are different from each other, and the user is prompted to select an examination request or display.

In this case, when the reference range at the other medical facility from which the second medical data (vital data) is extracted and the reference range at the own medical facility are different from each other, the display control function 158 displays a message P51 giving notification that the reference ranges are different from each other in a panel P5 corresponding to the extraction condition on the second medical data. In addition, the display control function 158 displays, in the panel P5, an operation element P52 through which an examination related to acquisition of the second medical data is requested, and an operation element P53 for instructing display of the second medical data.

The user of the medical information processing apparatus 100 checks the message P51 displayed in the panel P5, and operates the operation element P52 when desiring an examination request or operates the operation element P53 when desiring display of the second medical data. When the operation element P52 is operated, the examination request function 157 transmits the examination request information as described above. Accordingly, the user of the medical information processing apparatus 100 can request an examination for acquiring medical data of the same data type as that of the second medical data to a system in the own medical facility.

When the operation element P53 is operated, the display control function 158 displays the second medical data in the data display region G12, similarly to the case of FIG. 7 described above. The display control function 158 may directly display the second medical data or may display the second medical data in a different display form based on the reference ranges at the own medical facility and the other medical facility.

Second Modification

In the above-described embodiment, medical data to be extracted by the second extraction function 156 is medical data satisfying the extraction condition determined to be lacked by the first determination function 154, but is not limited thereto. For example, similarly to the first extraction function 153, the second extraction function 156 may extract medical data satisfying the extraction condition on a finding set by the finding setting function 152.

Accordingly, a medical professional can diagnose a subject while referring to pieces of medical data acquired under an identical extraction condition at the own medical facility and another medical facility, in other words, pieces of medical data of an identical data type with acquisition timings different from each other. Thus, the medical information processing apparatus 100 according to the present modification can provide the medical professional with an opportunity for multifaceted analysis on the medical data of the subject and thus can increase the usability of diagnosis support.

Third Modification

In the above-described embodiment, the first extraction function 153 and the second extraction function 156 extract medical data satisfying the extraction condition as a pair of a data type and an index value, but the extraction condition is not limited thereto. For example, among the pair of the data type and the index value, the first extraction function 153 and the second extraction function 156 may extract medical data satisfying a condition on the data type.

Accordingly, for example, the medical professional can consider the validity of a finding about a subject or the necessity for re-examination based on the relation between a measurement value and an index value included in the extracted medical data. Thus, the medical information processing apparatus 100 according to the present modification can provide the medical professional with an opportunity for multifaceted analysis on medical data of the subject and thus can increase the usability of diagnosis support.

Fourth Modification

In the above-described embodiment, the display control function 158 displays the first medical data extracted from the own medical facility and the second medical data extracted from another medical facility in panels different from each other, but is not limited thereto, and may display the first and second medical data in an identical panel. For example, when the first medical data and the second medical data are numerical data and can be displayed in graphs by using common coordinates, measured values included in both medical data may be displayed in graphs on the same coordinates. In this case, each measured value (graph) is preferably displayed in a state that allows identification of which medical facility the measured value is extracted from.

Fifth Modification

In the above-described embodiment, display arrangement of the screen G1 in which medical data is displayed is fixed or dynamically changeable, but may be set for each finding (extraction condition). In this case, for example, when display arrangement setting information (hereinafter referred to as display setting information) is stored in association with a finding set to a finding type in the extraction condition information 121 (refer to FIG. 3), the display arrangement can be switched between findings. The display setting information includes information defining the disposition position, panel size, and the like of each panel (display region) for displaying a piece of medical data corresponding to the extraction condition on the finding.

For example, in a case of the screen G1 described with reference to FIG. 6, the display setting information of "Finding 5" defines disposition of a large panel (panel P1) for displaying medication record data in the left region of the data display region G12, disposition of a small panel (panel P2) for displaying sample examination data at an upper part of the right region, and disposition of a small panel (panel P3) for displaying vital data at a lower part of the right region.

Functional components of the medical information processing apparatus 100 according to the present modification execute processing related to extraction of medical data and display of the screen G1 based on the above-described extraction condition information 121. Specifically, the first extraction function 153 extracts, based on the above-described extraction condition information 121, medical data satisfying the extraction condition on a finding set by the finding setting function 152 from among medical data of a subject managed at the own medical facility. The display control function 158 displays the first medical data extracted by the first extraction function 153 in a corresponding panel in the screen G1 (display arrangement). In addition, the display control function 158 displays, in a panel in which no medical data (first medical data) is to be displayed, an operation element for instructing acquisition of medical data related to a lacked extraction condition defined to be displayed in the panel from another medical facility, or an operation element for requesting an examination at the own medical facility. Then, when the second medical data is extracted by the second extraction function 156, the display control function 158 displays the second medical data in a corresponding panel in the screen G1 (display arrangement).

In this manner, in the present modification, the first medical data is displayed in a corresponding panel in the screen G1 based on the display arrangement set for each finding, and an operation element related to acquisition of lacked medical data is displayed in a corresponding panel in the screen G1. Accordingly, the medical information processing apparatus 100 allows the user of the medical information processing apparatus 100 to intuitively recognize the type of the lacked medical data, and can increase usability. In addition, since the operation element related to acquisition of the lacked medical data is displayed in the identical screen of the first medical data, the user of the medical information processing apparatus 100 can easily perform an operation related to acquisition of the lacked medical data without switching screens, which can lead to increase of usability.

As in the above-described embodiment, the display control function 158 may control display of various operation elements and display of a notification message based on a result of the determination by the first determination function 154 and the second determination function 155.

Sixth Modification

In the above-described embodiment, the second extraction function 156 extracts the second medical data from another medical facility, but a facility from which the medical data is extracted is not limited to a medical institution. For example, when a subject uses a measurement device such as an activity meter and a value measured by the measurement device is stored in a server device, a cloud, or the like, the second extraction function 156 may extract medical data (measured value) from a facility such as the server device or the cloud.

In this manner, the medical information processing apparatus 100 according to the present modification can collectively handle medical data of the subject managed at various facilities, and thus can efficiently collect medical data related to a finding without cumbersome work by a medical technician.

Seventh Modification

In the above-described embodiment, the medical information processing apparatus 100 have the finding estimation function 151, the finding setting function 152, the first extraction function 153, the first determination function 154, the second determination function 155, the second extraction function 156, the examination request function 157, and the display control function 158, but some or all of the functions may be provided in a device other than the medical information processing apparatus 100.

For example, the integrated data server 500 may have some or all of the above-described functions. In this case, the integrated data server 500 functions as a medical information processing apparatus and displays the above-described screens in the form of Web service or the like on the display 140 of the medical information processing apparatus 100. The medical information processing apparatus is not limited to one computer device but may be achieved by a plurality of computer devices connected with each other through a network. For example, the medical information processing apparatus may be achieved through cooperation of the integrated data servers 500 provided in the respective medical facility systems 10.

The above-described embodiment describes the example in which the finding estimation unit, the finding setting unit, the disposition unit, the first extraction unit, the determination unit, the second extraction unit, the examination request unit, and the display control unit in the present specification are achieved by the finding estimation function 151, the finding setting function 152, the first extraction function 153, the first determination function 154, the second determination function 155, the second extraction function 156, the examination request function 157, and the display control function 158, respectively, of the processing circuitry 150, but the embodiment is not limited thereto. For example, the finding estimation unit, the finding setting unit, the disposition unit, the first extraction unit, the determination unit, the second extraction unit, the examination request unit, and the display control unit in the present specification may be not only achieved by the finding estimation function 151, the finding setting function 152, the first extraction function 153, the first determination function 154, the second determination function 155, the second extraction function 156, the examination request function 157, and the display control function 158, which are described in the embodiment, but also achieved by hardware only or mixture of hardware and software.

The term "processor" used in the above description means, for example, a central processing unit (CPU), a graphics processing unit (GPU), or a circuit such as an application specific integrated circuit (ASIC) or a programmable logic device (for example, a simple programmable logic device (SPLD), a complex programmable logic device (CPLD), or a field programmable gate array (FPGA)). The processor achieves a function by reading and executing a computer program stored in the storage 120. Instead of being stored in the storage 120, the computer program may be directly incorporated in a circuit of the processor. In this case, the processor achieves the function by reading and executing the computer program incorporated in the circuit. The processor according to the present embodiment does not necessarily need to be configured by a single circuit but may be configured by a plurality of independent circuits combined as one processor to achieve the function of the processor.

The computer program executed by the processor is incorporated in a read only memory (ROM), the storage, or the like in advance and provided. The computer program may be recorded and provided as a file of a format installable or executable on these devices in a computer-readable storage medium such as a compact disc (CD) ROM, a flexible disk (FD), a CD recordable (CD-R), or a digital versatile disc (DVD). The computer program may be stored on a computer connected with a network such as the Internet and may be provided or distributed by downloading through the network. For example, the computer program is constituted by modules including the above-described functional components. Each module is loaded and generated on a main storage device when the CPU as actual hardware reads the computer program from the storage medium such as a ROM and executes the computer program.

According to at least one of the above-described embodiment and modifications, it is possible to increase the usability of acquisition of lacked medical data among medical data related to diagnosis of a subject.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:
   a storage that stores an extraction condition including, for each type of finding, at least one data type of medical data to be a basis of the finding and an index value of the at least one data type; and
   processing circuitry configured to:
      set, as a finding, an item related to diagnosis of a subject,
      extract, from medical data of the subject managed at a first facility, a piece of medical data of at least a part of the at least one data type included in the extraction condition corresponding to the finding of the subject,
      determine whether the data type of the extracted piece of medical data satisfies every data type included in the extraction condition corresponding to the finding of the subject,
      when the data type of the extracted piece of medical data does not satisfy every data type included in the extraction condition corresponding to the finding of the subject, further extract, according to the extraction condition, a piece of medical data of a lacked data type from medical data of the subject managed at a second facility other than the first facility,
      display on a screen the piece of medical data extracted from the first facility,
      when the piece of medical data of the lacked data type is extracted from the second facility, display in association with each other on the same screen (a) the piece of medical data extracted from the second facility and (b) information that identifies the second facility as a source of the extracted piece of medical data, and
      when, for the piece of medical data extracted from the second facility, a reference range concerning a determination of a health condition differs between the first facility and the second facility,
         add auxiliary information to the piece of medical data extracted from the second facility and display the auxiliary information, the auxiliary information indicating a first reference range of the first facility and a second reference range of the second facility, and
         correct a measured value of the piece of medical data extracted from the second facility based on a difference between the first reference range and the second reference range and display the corrected measured value.

2. The medical information processing apparatus according to claim 1, wherein the processing circuitry
   determines whether a piece of medical data of the lacked data type is available in the medical data of the subject managed at the second facility, and
   when it is determined that a piece of medical data of the lacked data type is available, displays on the screen an operation element through which display of the piece of medical data of the lacked data type is instructed.

3. The medical information processing apparatus according to claim 2, wherein, when the operation element is operated, the processing circuitry displays on the screen the piece of medical data extracted from the second facility.

4. The medical information processing apparatus according to claim 3, wherein, when the operation element is operated, the processing circuitry extracts the piece of medical data of the lacked data type from the second facility.

5. The medical information processing apparatus according to claim 2, wherein, when it is determined that no piece of medical data of the lacked data type is available in the medical data of the subject managed at the second facility, the processing circuitry displays on the screen information that gives notification of the lacked data type.

6. The medical information processing apparatus according to claim 2, wherein, when it is determined that no piece of medical data of the lacked data type is available in the medical data of the subject managed at the second facility, the processing circuitry displays on the screen an operation element through which examination related to acquisition of a piece of medical data of the lacked data type is requested.

7. The medical information processing apparatus according to claim 1, wherein the processing circuitry:
  estimates, as one or more finding candidates, one or more disease names corresponding to a physical characteristic included in the medical data of the subject, based on guideline information containing physical characteristics and disease names in association with each other,
  displays the one or more finding candidates in a selectable manner, and
  sets, when one of the one or more finding candidates is selected, the selected finding candidate as the finding of the subject.

8. The medical information processing apparatus according to claim 1, wherein the processing circuitry:
  estimates one or more finding candidates from the medical data of the subject using a machine learning model trained to learn a relation between medical data of a plurality of subjects and findings,
  displays the one or more finding candidates in a selectable manner, and
  sets, when one of the one or more finding candidates is selected, the selected finding candidate as the finding of the subject.

9. A medical information processing method comprising:
  setting, as a finding, an item related to diagnosis of a subject;
    extracting, by referring to a storage storing an extraction condition including, for each type of finding, at least one data type of medical data to be a basis of the finding and an index value of the at least one data type, from medical data of the subject managed at a first facility, a piece of medical data of at least a part of the at least one data type included in the extraction condition corresponding to the finding of the subject;
    determining whether the data type of the extracted piece of medical data satisfies every data type included in the extraction condition corresponding to the finding of the subject; and
    in response to the data type of the extracted piece of medical data not satisfying every data type included in the extraction condition corresponding to the finding of the subject, further extracting a piece of medical data of a lacked data type from medical data of the subject managed at a second facility other than the first facility;
    displaying on a screen the piece of medical data extracted from the first facility;
    after the piece of medical data of the lacked data type is extracted from the second facility, displaying in association with each other also on the screen (a) the piece of medical data extracted from the second facility and (b) information that identifies the second facility as a source of the extracted piece of medical data, and
    in response to, for the piece of medical data extracted from the second facility, a reference range concerning a determination of a health condition differing between the first facility and the second facility,
      adding auxiliary information to the piece of medical data extracted from the second facility and displaying the auxiliary information, the auxiliary information indicating a first reference range of the first facility and a second reference range of the second facility, and
      correcting a measured value of the piece of medical data extracted from the second facility based on a difference between the first reference range and the second reference range and displaying the corrected measured value.

10. The medical information processing apparatus according to claim 1, wherein the processing circuitry:
  disposes, for each data type corresponding to the finding of the subject, a display region for displaying medical data of the data type on the screen, and
  displays the pieces of medical data extracted from the first facility and the second facility in the respective display regions for displaying medical data of the respective data types.

* * * * *